United States Patent [19]
Mahoney

[11] Patent Number: 5,788,633
[45] Date of Patent: Aug. 4, 1998

[54] ECG ELECTRODE STRIP WITH ELONGATED SLOTS

[75] Inventor: Steven A. Mahoney. McMinnville, Oreg.

[73] Assignee: Hewlett-Packard Company. Palo Alto, Calif.

[21] Appl. No.: 789,576

[22] Filed: Jan. 28, 1997

[51] Int. Cl.⁶ .................................................. A61B 5/0408
[52] U.S. Cl. .......................... 600/382; 600/391; 600/392; 600/393; 600/39
[58] Field of Search ...................... 600/382, 386, 600/388, 389, 390, 391, 392, 393, 397; 607/149, 152, 153

[56] References Cited

U.S. PATENT DOCUMENTS

| | | |
|---|---|---|
| 3,476,104 | 11/1969 | Davis . |
| 4,033,333 | 7/1977 | DeSalvo et al. . |
| 4,202,344 | 5/1980 | Mills et al. . |
| 4,233,987 | 11/1980 | Feingold . |
| 4,353,372 | 10/1982 | Ayer . |
| 4,583,549 | 4/1986 | Manoli . |
| 4,733,670 | 3/1988 | Hays et al. . |
| 4,832,608 | 5/1989 | Kroll . |
| 4,957,109 | 9/1990 | Groeger et al. . |
| 5,042,481 | 8/1991 | Suzuki et al. . |
| 5,168,875 | 12/1992 | Mitchiner . |
| 5,184,620 | 2/1993 | Cudahy et al. . |
| 5,191,886 | 3/1993 | Paeth et al. . |
| 5,224,479 | 7/1993 | Sekine . |
| 5,257,631 | 11/1993 | Wilk . |
| 5,327,888 | 7/1994 | Imran . |
| 5,341,806 | 8/1994 | Gadsby et al. . |
| 5,445,149 | 8/1995 | Rotolo et al. . |
| 5,507,290 | 4/1996 | Kelly et al. . |

Primary Examiner—Lee S. Cohen

[57] ABSTRACT

An ECG harness is positioned on the chest of patient for making electrocardiographic measurements. The harness includes a strip of nonconductive film having a plurality of slots spaced along the length of the strip at selected anatomical positions. A connector terminal is formed at one edge of the strip for connection to a monitoring device. Electrically conductive border traces extend around the slots. The border traces are exposed on the outer side of the strip and insulated from the inner side of the strip. Conductive leads extend from the connector terminal to the border traces. Electrode pads are placed on the outer side of the strip at least partially extending over the slots. Each of the electrode pads has a conductive inner side for electrical contact with one of the border traces and the skin of the patient.

13 Claims, 2 Drawing Sheets

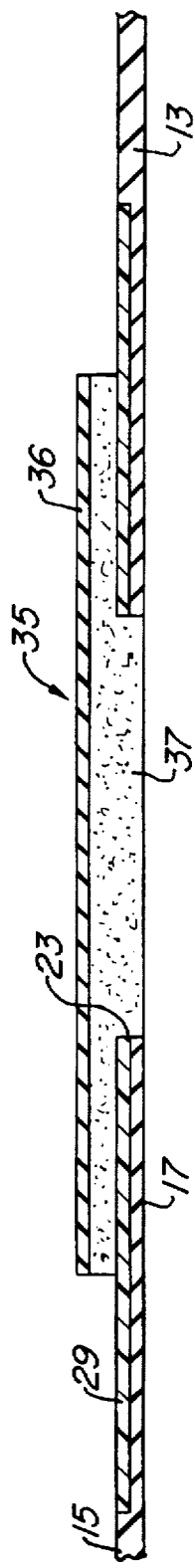
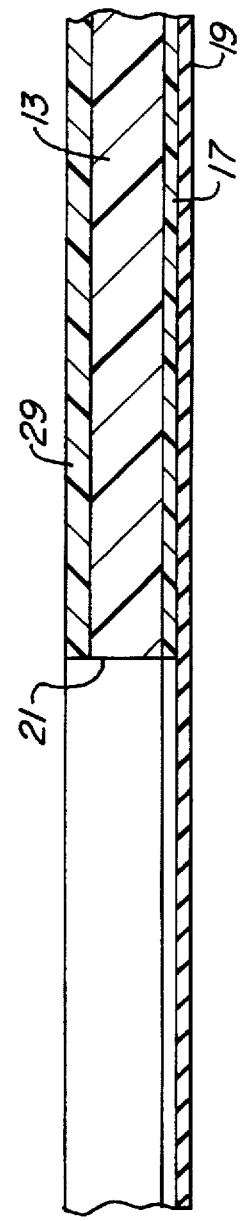

5,788,633

ECG ELECTRODE STRIP WITH ELONGATED SLOTS

FIELD OF THE INVENTION

This invention relates generally to sensors for conducting electrocardiograph measurements, and in particular to a harness that facilitates rapid and proper placement of the electrodes on a patient.

BACKGROUND OF THE INVENTION

Electrocardiograph measurements ("ECG") are commonly made to provide information about a patient's heart performance. Typically a technician will place sensors on a patient's chest. The sensors are electrodes having an adhesive gel for adhering to the skin of the patient as well as for providing electrical conductivity. The technician then clips leads from an ECG monitor to a terminal on each of electrode pads. The technician will monitor voltage differential to provide a chart indicating the condition of the patient's heart.

It is important to place the electrode pads at fairly precise anatomical positions. These positions have been established so as to provide adequate comparisons with ECG measurements that have been taken across a wide variety of patients. However, varieties in patient size makes this placement a difficult task. Normally, six of the electrode pads must be positioned, then clipped to the leads. Furthermore, the technician has to be careful to clip the proper leads to the proper electrode pads.

Skill and care are required to be able to properly position the sensors for an ECG measurement. This become a more difficult task during emergencies. For example, ECG measurements made in an ambulance or with a portable ECG device at a field site are very informative. With time of the essence, it is a difficult task to properly and quickly place and connect the electrode pads.

Prior art patents show a variety of devices for facilitating ECG measurements. Generally these devices include some type of strip or harness with the electrodes being prewired to a connector terminal on an edge of the strip. Preconnecting the electrode pads to a connector terminal reduces the chances for a technician to switch the leads inadvertently. Also, some of the devices place the electrodes in the general vicinity of the desired anatomical position. However, because of the differences in patient size, a variety of sizes of these strips may need to be kept on hand. Some of the devices shown would appear to be expensive. For one reason or another, such prewired strips are not commonly used.

SUMMARY OF THE INVENTION

In this invention, a harness is provided for positioning on the chest of a patent for making ECG measurements. The harness includes a thin strip of nonconductive film which has a plurality of slots. The slots are positioned for placement at preselected anatomical positions. The strip has an inner side containing an adhesive layer for adhering to the skin of a patient. A terminal connector is located at one edge of the strip for connection to a monitoring device.

A plurality of electrically conductive border traces extend at least partially around the slots. The border traces are exposed on an outer side of the strip and insulated from the inner side of the strip. Conductive leads or traces are formed on the strip also. At least some of the conductive leads extend from the border traces to connect the border traces with the connector terminals.

Electrode pads are provided separately from the strip. The electrode pads are generally of conventional nature, but do not require an allegator clip terminal. The pads have a conductive gel on an inner side. The pads are placed over at least portions of the slots in electrical contact with the border traces. The conductive gel of the pads places the skin of the patient in electrical continuity with the border traces and the conductive leads.

To avoid having a large number of sizes, some of the slots are elongated, having a greater length than a width. The electrode pads have a width and length, but both are substantially less than the length of the elongated slots. This allows the technician to selectively place the pad at different points along the slots depending upon the size of the patient.

BRIEF DESCRIPTION OF THE DRAWING

FIG. 2 is an enlarged sectional view of a portion of the ECG harness taken along the line 2—2 of FIG. 1, with the thickness greatly exaggerated.

FIG. 3 is a further enlarged sectional view of the harness of FIG. 1, taken along the line 3—3 of FIG. 1, with the thickness greatly exaggerated.

DETAILED DESCRIPTION OF A PREFERRED EMBODIMENT

Figure 1:
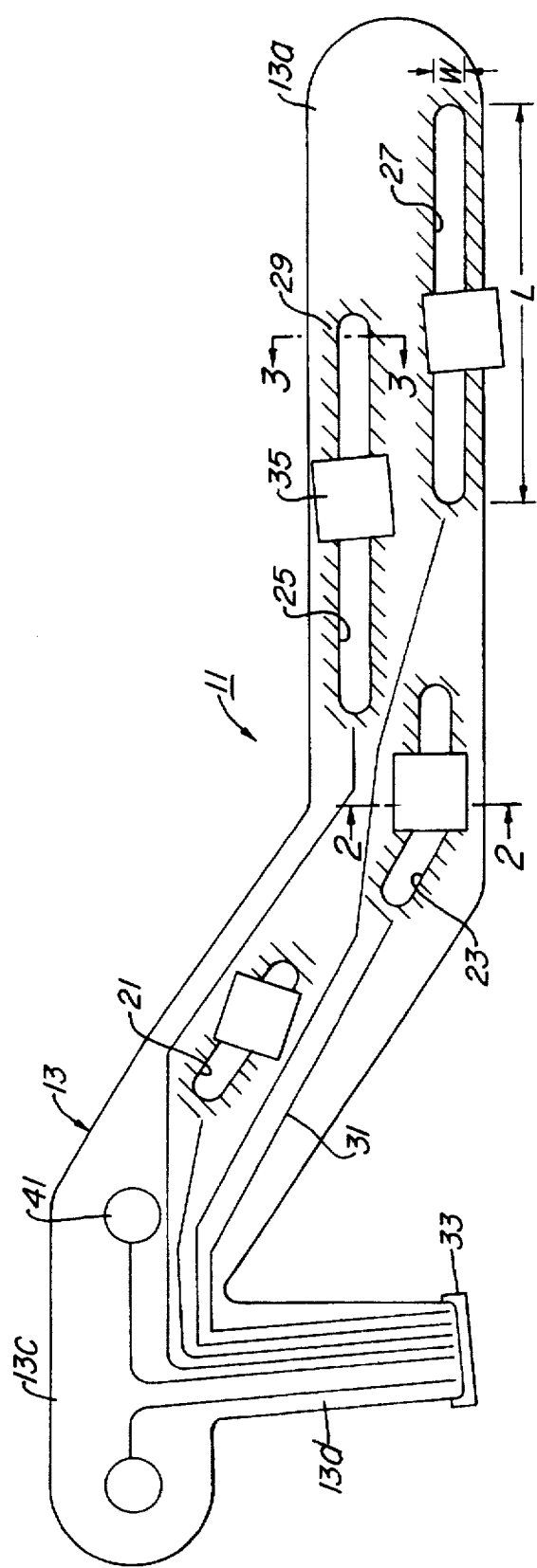
FIG. 1 is an elevational view schematically illustrating an ECG harness constructed in accordance with this invention.

Referring to FIG. 1, a harness 11 is shown for placement on a patient for making ECG measurements. Harness 11 includes a flexible strip 13. Strip 13 is of a nonconductive substrate or film and has a configuration to perform ECG measurements on a wide variety of patient sizes. Strip 13 has a straight lateral portion 13a which leads to a diagonal portion 13b which is at an obtuse angle relative to lateral portion 13a. Diagonal portion 13b is straight and leads to a head portion 13c. A terminal portion 13d extends from head portion 13c approximately perpendicular to lateral portion 13a. Strip 13 is elongated, having a length from head portion 13c to the free edge of lateral portion 13a that is considerably greater than its width.

Referring to FIG. 2, strip 13 is considerably thinner than as shown and is exaggerated in thickness. Strip 13 has an outer side 15 that will face away from the patient and an inner side containing an adhesive coating 17. As illustrated in FIG. 3, a backing layer 19 will cover adhesive side 17 until use. Backing layer 19 is a removable film for protecting adhesive side 17.

Referring again to FIG. 1, strip 13 has a plurality of elongated slots 21, 23, 25 and 27 which extend completely through strip 13. Each slot has a length L that is greater than its width W. However, slots, 21, 23, 25, 27 are not all straight and not all the same in length. The width W is preferably the same. Slot 23 is formed in a dogleg shape because it is located approximately at the junction of diagonal portion 13b with lateral portion 13a. Slot 21 is less in length than the lengths of slots 25 and 27 in the embodiment shown because it is closer to head portion 13c than the others. The reason for the different lengths of slots 21, 23, 25 and 27 is to accommodate a great variety of desired anatomical positions for different sizes of patients.

Each slot 21, 23, 25 and 27 is surrounded by a border trace 29. Border traces 29 are electrically conductive and form perimeters around each slot 21, 23, 25 and 27. Border traces 29 are formed in the substrate of strip 13 in a conventional manner such as by silver chloride deposition. As shown in FIGS. 2 and 3, border traces 29 are exposed on the outer side 15 of strip 13. However, border traces 29 are insulated from inner side 17 by portions of nonconductive strip 13.

Harness 11 has a plurality of conductive leads 31. Leads 31 are formed also of a conductive ink such as silver chloride in the same manner of border traces 29. Leads 31 also do not extend through the entire thickness of strip 13. Conductive leads 31 may be exposed to outer side 15, but they must not be exposed to adhesive side 17. Leads 31 extend from a connector terminal 33 which is a conventional connector for electrically connecting harness 11 to a ECG monitor. One of the leads 31 will extend to each of the border traces 29 to electrically and separately connect border traces 29 to connector terminal 33.

A plurality of electrode pads 35 are employed with strip 13. Electrode pads 35 may be of a conventional type commonly used for ECG measurements. However, they need no terminal for connecting to an alligator clip as in the prior art. Each electrode pad 35 as shown in FIG. 2 has a conventional conductive layer 36 which may be a conductive ink deposited on a film. A conductive gel 37 is coated on the inner side of conductive layer 36 to electrically connect skin of the patient to conductive layer 36. Gel 37 is sufficiently thick so as to extrude through portions of slots 21, 23, 25, 27. Also, some of the gel 37 will contact border traces 29. Preferably gel 37 contains an adhesive component so as to adhere to border traces 29 and to the skin of a patient.

As shown in FIG. 1, electrode pads 35 are much smaller in side to side dimension than the length L of each of the slots 21, 23, 25, 27. Electrode pads 35 are shown as being square, having a length and width the same, although the configuration could vary and could be circular as well. One of the length and width dimensions of electrode pad 35 is preferably greater than the width W, but both dimensions are less than slot length L. Electrode pads 35 can be positioned at a variety of points along the length L of the slots 21, 23, 25, 27. Furthermore, because of the greater vertical dimension of each electrode pad 35 than the width W, each electrode pad 35 will extend completely across of each slot 21, 23, 25 and 27.

Not all of the leads 31 lead to one of the slots 21, 23, 25 or 27 in the preferred embodiment. Rather, two of the leads 31 lead to fixed electrodes 41. Electrodes 41 are integrally formed with strip 13 and have coatings of conductive gel. Removing backing layer 19 exposes inner sides of fixed electrodes 41 to the skin of the patient.

In use, backing layer 19 will be peeled of f and strip 13 placed on the chest of the patient in a desired orientation. Adhesive layer 17 will bond strip 13 to the patient. Fixed electrodes 41 will be placed at the desired anatomical position. The technician will then place each of the electrode pads 35 into position. First the technician will remove a backing layer (not shown) on each pad 35 to expose gel 37. The technician will then place pads 35 a t desired points along the length L of each of the slots 21, 23, 25, 27. When doing so, a portion of the gel 37 will come into electrical contact with the patient's skin as well as coming into electrical contact with border traces 27. Preferably each electrode pad 35 will extend across the full width W of each of the slots 21, 23, 25 and 27. The technician then connects connector terminal 33 to an ECG monitor and conducts the test. For hospital use, nor mall y harness 11 will be disposable.

The invention has significant advantages. Being prewired, the harness eliminates inadvertently switching of leads which can occur with the conventional prior art ECG technique. The harness will fit a variety of patient sizes because of the elongated slots. The orientation of the slots and the configuration of the strip assures fairly precise anatomical positioning of the electrodes. This speeds up the process greatly for emergency applications, and reduces the level of skill required for the technician. It also allows non professionals to administer an ECG test at home. The harness is inexpensive and may be disposable.

I claim:

1. A harness for positioning on a chest of a patient for use with electrode pads which have conductive inner sides to make electrocardiographic measurements, comprising:

a strip of a nonconductive film having a plurality of slots positioned for placement at selected anatomical positions;

a connector terminal at one edge of the strip for connection to a monitoring device;

a plurality of electrically conductive border traces, each formed on the strip and extending at least partially around one of the slots, the border traces being insulated from an inner side of the strip to avoid contact with the skin of the patient;

a plurality of conductive leads formed on the strip, each leading from the connector terminal, at least some of the leads leading to the border traces to electrically connect the border traces with the connector terminal; and wherein each of the border traces is exposed on an outer side of the strip for electrical engagement with the conductive inner side of one of the electrode pads which may be selectively placed on the outer side of the strip at least partially extending over one of the slots so as to place the conductive inner side of the electrode pad in electrical contact with one of the border traces and in electrical contact with the skin of the patient.

2. The harness according to claim 1 wherein:

at least one of the slots is elongated with a length longer than a width, referred to as an elongated slot, allowing selective placement of one of the electrode pads along the length of the elongated slot.

3. The harness according to claim 1 wherein the strip has an inner side containing an adhesive layer for adhering to skin of a patient.

4. A harness for positioning on a chest of a patient for making electrocardiographic measurements:

a strip of a nonconductive film having a plurality of slots positioned for placement at selected anatomical positions;

a connector terminal at one edge of the strip for connection to a monitoring device;

a plurality of electrically conductive border traces, each formed on the strip and extending at least partially around one of the slots, the border traces being exposed on an outer side of the strip and insulated from an inner side of the strip to avoid contact with the skin of the patient;

a plurality of conductive leads formed on the strip, each leading from the connector terminal, at least some of the leads leading to the border traces to electrically connect the border traces with the connector terminal; and a plurality of electrode pads, each selectively placed on the outer side of the strip at least partially extending over one of the slots, each of the electrode pads having a conductive inner side in electrical contact with one of the border traces and for electrical contact with the skin of the patient.

5. The harness according to claim 4 wherein:

at least one of the slots is elongated with a length longer than a width, referred to as an elongated slot; and each of the electrode pads has a width and a length, both of which are shorter than the length of the elongated slot, allowing selective placement of one of the electrode pads along the length of the elongated slot.

6. The harness according to claim 4 wherein the inner side of the electrode pads comprises an electrically conductive gel.

7. The harness according to claim 4 wherein the strip has an inner side containing an adhesive layer for adhering to skin of a patient.

8. The harness according to claim 4 wherein:

the slots are elongated with lengths longer than widths; and each of the electrode pads has a width dimension and a length dimension, both dimension being shorter than the lengths of the slots, allowing selective placement of the electrode pads along the lengths, and one of the dimensions of each of the electrode pads is greater than the widths of the slots.

9. A harness for positioning on a chest of a patient for making electrocardiographic measurements:

a flexible strip of a nonconductive film having a plurality of slots positioned for placement at selected anatomical positions, the slots being elongated with lengths greater than widths, the strip having an inner side containing an adhesive layer for adhering to skin of a patient;

a connector terminal at one edge of the strip for connection to a monitoring device;

a plurality of electrically conductive border traces, each formed on the strip and extending around one of the slots, the border traces being exposed on an outer side of the strip and insulated from the inner side of the strip to avoid contact with the skin of the patient;

a plurality of conductive leads formed on the strip, each leading from the connector terminal, at least some of the leads leading to the border traces to electrically connect the border traces with the connector terminal; and a plurality of electrode pads, each selectively placed on the outer side of the strip at least partially extending over one of the slots, each of the electrode pads having a conductive inner side for electrical contact with one of the border traces and for electrical contact with the skin of the patient, each of the electrode pads having length dimension and a width dimension, both of which are shorter than the lengths of the slots so as to allow selective placement of the electrode pads along the lengths of the slots.

10. The harness according to claim 9 wherein at least one of the dimensions of the pads is greater than the widths of the slots.

11. The harness according to claim 9 wherein the inner side of the electrode pads comprises an electrically conductive adhesive gel.

12. A method of placing sensors on a patient for an electrocardiograph measurement, comprising:

(a) providing a strip of a nonconductive film having a plurality of slots, a connector terminal at one edge of the strip, a plurality of conductive leads leading from the connector terminal, at least some of the leads leading to the slots and being electrically exposed to an outer side of the strip at the slots;

(b) placing the strip on a chest of a patient;

(c) providing a plurality of electrode pads, each having a conductive inner side;

(d) securing the electrode pads on the outer side of the strip, each at least partially extending over one of the slots, with the inner side of each of the electrode pads in electrical contact with one of the leads and in electrical contact with the skin of the patient; and (e) connecting the connector terminal to a monitor.

13. The method according to claim 12, wherein:

step (a) comprises providing the slots with lengths greater than widths;

step (c) comprises providing the electrode pads with length and width dimensions, at least one of which is shorter than the lengths of the slots; and step (d) comprising selectively positioning the electrode pads along the lengths of the slots.

* * * * *